(12) United States Patent
Ellingsen

(10) Patent No.: US 7,048,732 B2
(45) Date of Patent: May 23, 2006

(54) FIBER OPTIC PROBE FOR TEMPERATURE MEASUREMENTS IN BIOLOGICAL MEDIA

(75) Inventor: Reinold Ellingsen, Heimdal (NO)

(73) Assignee: Optomed AS, Trondheim (NO)

( * ) Notice: Subject to any disclaimer, the term of this patent is extended or adjusted under 35 U.S.C. 154(b) by 268 days.

(21) Appl. No.: 10/093,814

(22) Filed: Mar. 11, 2002

(65) Prior Publication Data

US 2002/0147394 A1 Oct. 10, 2002

Related U.S. Application Data

(63) Continuation-in-part of application No. PCT/NO00/00291, filed on Sep. 7, 2000.

(30) Foreign Application Priority Data

Sep. 9, 1999 (NO) ................................. 19994363

(51) Int. Cl.
*G02B 6/124* (2006.01)
(52) U.S. Cl. ........................................ 606/20; 385/12
(58) Field of Classification Search ................ 600/412, 600/414; 606/20–26, 2–13, 412, 414; 385/12, 385/13
See application file for complete search history.

(56) References Cited

U.S. PATENT DOCUMENTS

| 4,016,761 | A |  | 4/1977 | Rozzell et al. |
| 4,245,507 | A |  | 1/1981 | Samulski |
| 4,626,110 | A |  | 12/1986 | Wickersheim et al. |
| 4,996,419 | A |  | 2/1991 | Morey |
| 5,355,423 | A |  | 10/1994 | Phillips |
| 5,394,457 | A | * | 2/1995 | Leibinger et al. ............ 378/162 |
| 5,513,913 | A |  | 5/1996 | Ball et al. |
| 5,895,401 | A |  | 4/1999 | Daum et al. |
| 6,039,730 | A | * | 3/2000 | Rabin et al. ................... 606/23 |
| 6,125,216 | A | * | 9/2000 | Haran et al. ................... 385/12 |

FOREIGN PATENT DOCUMENTS

| EP | 0672914 A1 | 9/1995 |
| EP | 0870463 A2 | 10/1998 |

OTHER PUBLICATIONS

Rao, Yun-Jiang, et al., "In-Fiber Bragg-Grating Temperature Sensor System for Medical Applications", *Journal of Lightwave Technology*, May 1997, pp. 779-785, vol. 15, No. 5, IEEE.

Rao, Y.J., et a., "Optical In-Fiber Bragg Grating Sensor Systems for Medical Applications", *Journal of Biomedical Optics*, Jan. 1998, pp. 38-44, vol. 3, No. 1.

* cited by examiner

*Primary Examiner*—Roy D. Gibson
*Assistant Examiner*—Aaron Roane
(74) *Attorney, Agent, or Firm*—Rothwell, Figg, Ernst & Manbeck, PC

(57) ABSTRACT

The invention relates to an insertion probe for sensing distributed temperature comprising a tube containing at least one optical fiber being inscribed with at least one Bragg grating, the tube being sealed at its distal end. The probe is characterized in that it consists of materials having low magnetic susceptibility. The invention also relates to the use of such a probe in cryosurgery to allow the use of magnetic resonance imaging.

23 Claims, 1 Drawing Sheet

FIBER OPTIC PROBE FOR TEMPERATURE MEASUREMENTS IN BIOLOGICAL MEDIA

This application is a continuation-in-part of International application no. PCT/NO00/00291, filed Sep. 7, 2000.

FIELD OF THE INVENTION

This invention relates to an insertion probe and the use of this for sensing temperature, particularly during cryosurgery.

BACKGROUND

Thermal energy in interaction with biological matter is being used both in medicine and in the food processing industry. Exchange of thermal energy inside any system or between systems involves heat transfer processes that in turn affect the local temperature and its temporal and spatial distribution. Bioheat transfer analysis in living systems is generally complicated by the fact that the thermal properties are generally nonhomogeneous and anisotropic with considerable variations intra and inter specimen samples. Biological matter responds to the exposure of temperature changes in different ways. Consequently it might be argued that in situ monitoring of the thermal profile inside some confined volume during these procedures is of interest in a variety of applications.

Electromagnetic (EM) fields, from visible and infrared (IR) light to microwave and radio frequency (RF) waves are frequently applied under these circumstances serving as the energy carrier or as the imaging information carrier as is the case in the magnetic resonance (MR) imaging. Strong EM fields disqualify conventional electronic sensors due to absorption of EM energy and induced currents, while fiber optical sensors are dielectric in nature and intrinsically immune to the same fields. It is thus an object to this invention to provide a probe which may be used inside a body being subject to strong EM fields.

Electronic sensors for temperature measurements do not offer immunity versus electromagnetic fields and consequently, precautions have to be taken for effective shielding if they are to be applied under high EM field circumstances.

In Y. Rao, D. J. Webb, D. A. Jackson, L. Zhang, and I. Bennion, "In-Fiber Bragg-Grating Sensor System for Medical Applications", J. Lightwave Technol., Vol. 15, No. 5, pp. 779–785, 1997 a sensor system is described for use in a human body. No precautions are taken in this case to enable the probe to be used under high EM circumstances. Also, the sensor is not prepared for use at temperatures below −40° C. or above +80°. The tube material, polyamide or nylon, limits the sensor to a temperature range between −40° C. and +80° C. Another disadvantage is that the sensor fiber is in direct physical contact with the environment into which its sheath is inserted through apertures arranged in the wall of the sheath next to each FBG sensor element. Thus biologic solvents will intrude into the lumen of the sheath and possibly influence the stress condition of the fiber. Also, index matching gel is applied at the end of the sensor fiber inside the sheath. The gel will solidify by freezing at low temperatures, causing the fiber to stick to the sheath tubing. Thus this sensor does not comply with precise measurements over a large temperature range.

One particularly important application where temperature monitoring is critical is the expanding field of cryosurgery. Cryosurgery is becoming an important modality for treating a number of varied conditions. One common example is the treatment of prostate cancer by freezing the prostate gland to a sufficiently low temperature to kill the cells within, to ensure that any cancerous cells therein are killed.

To date performing such procedures has been difficult and required great skill on the part of the physician carrying them out. The difficulty is that the physician must ensure that all potentially cancerous cells are killed by being frozen whilst avoiding damage to surrounding tissue and structures such as the rectal wall.

It is therefore a further object of the present invention to provide an improved method of cyrosurgery.

As has been described above, conventional temperature probes cannot be used in conjunction with imaging which utilises high electro-magnetic fields such as Magnetic Resonance Imaging (MRI). This compounds the difficulty in cryosurgical applications of being able to control the freezing process since ultrasound imaging which is used instead can only image the edges of the ice ball formed. The ice ball appears as a uniform dark area on the ultrasound image and thus gives no information on temperature within the ice ball. It has been shown that, under some circumstances, water can be super-cooled to approximately −45° degrees Centigrade. Thus, the presence of an ice ball is no guarantee that all cells within it boundaries have been killed.

U.S. Pat. No. 5,647,848 to Chinn, the full contents of which are explicitly incorporated herein by reference, describes this problem and seeks to solve it by the use of an increased number of temperature probes. These are, however of the conventional sort and ultrasound imaging must therefore still be used.

SUMMARY

The present invention provides an insertion probe and the use of this for sensing temperature using at least one optical fiber, each inscribed with at least one Bragg grating being loosely positioned in a tube so as to allow the fiber(s) to expand and contract freely with changing temperatures, the tube being sealed in both ends.

The present invention also provides a method of cryosurgery utilising such probes which allows magnetic resonance imaging to be used. This can provide better spatial and temperature resolution than ultrasound.

Fiber Bragg gratings (FBG) may be written into the core of an optical fiber at any predetermined position along the fiber with spacings down to 1 mm and minimum grating lengths of 1–2 mm. Thus a temperature distribution sensor may be tailored to the thermal gradients or thermal profile of the measured body. The spacing between the sensor elements may not be equidistant. The effective density of the FBG's along the probe may be increased by increasing the number of sensor fibers. Fiber Bragg gratings are well known within the art, an example of a sensor with accompanying measuring systems are described in U.S. Pat. No. 6,097,487.

It is an additional object of this invention to provide an insertion probe assembly based on fiber optics which is designed for the measurement of distributed temperature in biological matter over a temperature range spanning from −200° C. to +100° C. during the simultaneous exposure to strong electromagnetic fields. Thus the same probe may be used in relation to hyperthermia, being subject to temperatures between 37° C. and 55° C., in diathermy with temperatures up to 100° C. and in cryotherapy in which the temperature may be monitored within a range from −180° C. to +40° C. Using the same type of probe in all of these cases reduces the need for specialized instruments and thus reduces the costs for hospitals and other medical institutions.

It is also an object of this invention to provide a probe being suitable for insertion into biological materials typically with high contents of water, e.g. into the canals and cavities of a body such as bronchia, urinary/gall bladder, alimentary canal, urogenital organs and cardiovascular system.

The insertion probe assembly is essentially one or more optical fibers, into which a number of Fiber Bragg Grating (FBG) sensor elements are inscribed, loosely arranged in a tube serving as mechanical support and chemical shield with respect to the biological matter environment. The tube is closed at its distal end. This sensor is designed for thermal measurements, thus it is important to de-couple the optical fiber or fibers from changes in mechanical stress and strain transferred from the walls of the shield tube. A loose tube gives the sufficient de-coupling and represents as well a barrier against water intrusion. Especially during application at freezing temperatures it is essential that the moisture content inside the tube is low in order to avoid the fiber or fibers from sticking to the tube wall and thereby produce erroneous measurements. More specific, the probe according to the invention is characterized as stated in the independent claims.

It is a further object of the invention to provide a method of cryosurgery which does not require the use of ultrasound imaging.

When viewed from a further aspect, the invention provides a method of performing cryosurgery on a living body comprising the steps of:

inserting one or more insertion probes into said living body, said insertion probe(s) comprising a tube containing at least one optical fiber being inscribed with at least one Bragg grating, the tube being sealed at its distal end, and wherein said temperature insertion probe(s) consist of materials having low magnetic susceptibility; and sensing a distributed temperature of a part of said living body using said insertion probe(s).

Preferably the method comprises the step of imaging said living body using magnetic resonance imaging.

When viewed from a further aspect, the invention provides a cryosurgical system for treating a part of a living body, the system comprising:

one or more cryo-applicators for cryosurgically cooling said part of said living body;

at least one temperature probe for insertion into said living body, comprising a tube containing at least one optical fiber being inscribed with at least one Bragg grating, the tube being sealed at its distal end, and wherein said temperature probe comprises substantially materials having low magnetic susceptibility;

magnetic resonance imaging apparatus for imaging said part of said living body; and a temperature display connected to said temperature probe(s) for displaying the temperature of said part of said living body or a surrounding part.

The invention also provides a method for cryosurgically treating a part of a living body comprising the steps of:

cooling a part of a living body;

measuring a temperature within said part of said living body or a surrounding part as said part is cooled, using one or more optical temperature probes having a low magnetic susceptibility;

imaging said part of said living body using magnetic resonance imaging;

thereby to monitor and control a degree of cooling applied to the part of the living body.

Preferably said optical probe(s) comprises a tube containing at least one optical fiber being inscribed with at least one Bragg grating, the tube being sealed at its distal end.

The invention will be described below with reference to the accompanying drawing, which illustrates a preferred embodiment of the invention by way of example.

DETAILED DESCRIPTION OF PREFERRED EMBODIMENTS

Figure 1:
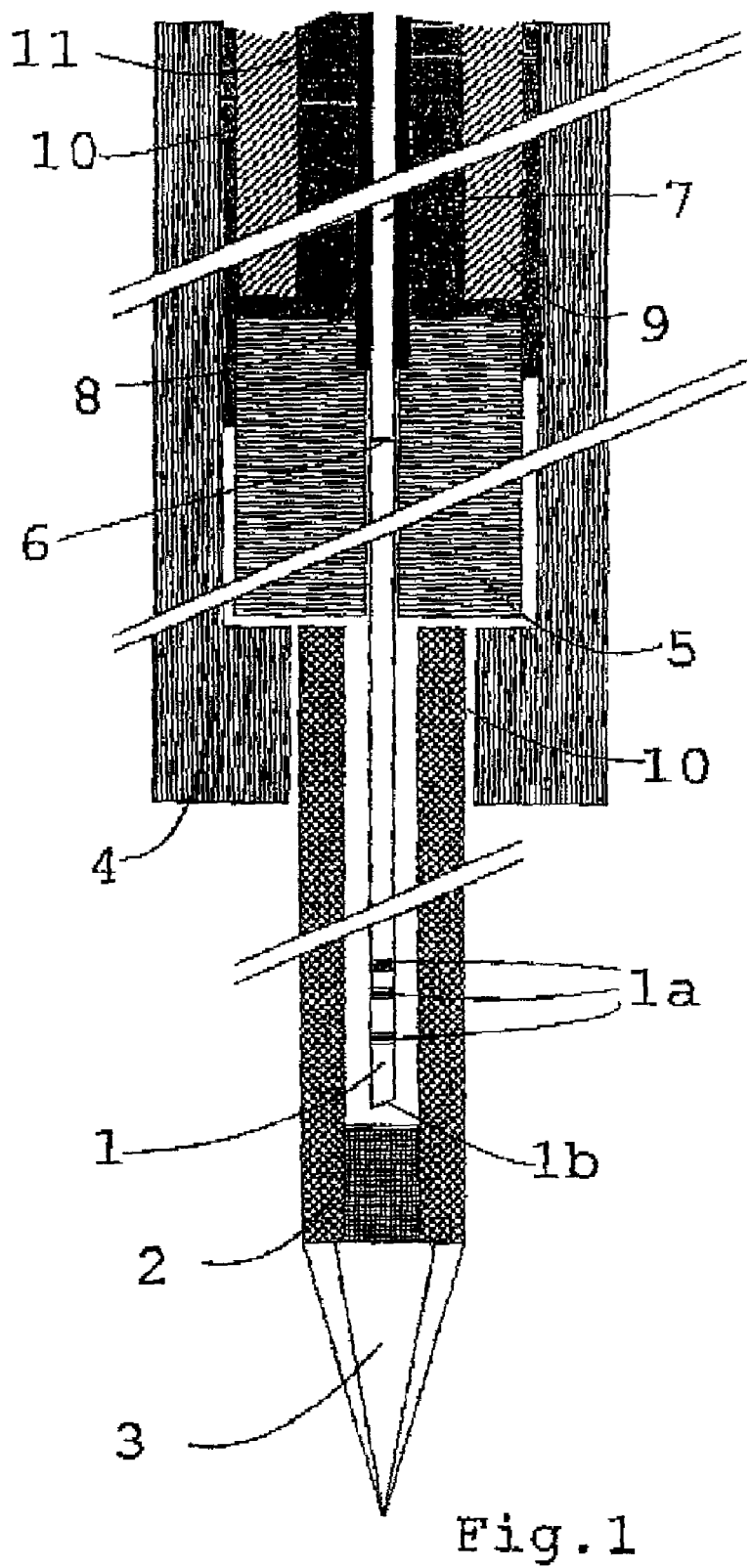
FIG. 1 illustrates a longitudinal section of a probe according to the invention, being provided with means for connecting to measuring instruments.

In the embodiment shown in the drawing a single optical fiber sensor 1 is provided within a tube 2. The optical fiber sensor 1 comprises at least one Bragg grating 1a and may be connected to available measuring instruments for analysing signals reflected in the fiber, thus e.g. to obtain the temperature at chosen positions. The sensor and related systems may be of any available type, e.g. as described in the abovementioned U.S. Pat. No. 6,097,487, and will not be described in any further detail here.

By using a Fiber Bragg sensor with a number of sensor points the probe is capable of monitoring the temperature at one or more positions in a body, e.g. monitoring the thermal profile in processing food during heating and freezing. Using the probe according to the invention these measurements are indifferent to the method of energy transfer into the body.

The distal end 1b of the fiberoptic sensor 1 is wedge cut to reduce reflections from the end, and the fiber is arranged loosely in the tube so as to be free to expand and contract with the changes in temperature, thus allowing for used in a large variety of temperatures without inducing mechanical stress on the fiber sensor 1. The end 1a of the fiber 1 is usually positioned approximately 1 mm from the tip 3 of the probe, so as to avoid contact between the parts even if the length of the fiber 1 changes relative to the length of the tube 2.

In the shown embodiment the distal end of the tube 2 is closed with a cutting sharp tip 3 thereby preventing water intrusion, and also providing a possibility insert the probe into biological materials. The tip 3 may also be rounded or flat if the cutting edge is not necessary e.g. when following the natural tubes of the body, or if there is a risk of puncturing vital organs, veins etc. The tip 3 may be fastened to the tube 2 using an adhesive or similar, or may be manufactured as an integral part of the tube, thus sealing it is in the process.

The tube 2 and the tip 3 of the probe is made from a material having a low magnetic susceptibility, so as to provide for use during measurements involving use of strong electromagnetic fields. The magnetic susceptibility of the used materials should be below 200 ppm, for example titanium may be used, which has a magnetic susceptibility being slightly less than 200 ppm, and preferably below 10 ppm, for example polymeric plastics such as polyimid, teflon and nylon. In some cases the magnetic susceptibility may, however, be as high as 300 ppm. Depending on the materials magnetic susceptibilities being 100 ppm or 50 ppm may of course also be used.

If the susceptibility is in the higher region of this range the probe may be seen in the MR measurements. This may be advantageous if the exact position of the measured temperatures is to be found. If the probe material has a magnetic susceptibility below 10 it may be provided with metallic markers, e.g. rings, or other materials having a relatively higher magnetic susceptibility than the rest of the probe material, fastened to the probe, so as to give easily recognisable features in the MR measurements. Such rings are not shown in the drawings, but may be positioned at any point along the tube, e.g. indicating the approximate positions of the Bragg gratings in the optical fiber inside the tube. The abovementioned rings may thus be made from titanium and the housing and sensor be made from a material having a lower magnetic susceptibility. The materials in which the tube 2 and the tip 3 is made may be chosen within a wide range of different materials having sufficiently low magnetic susceptibility and being capable of withstanding a large range of temperatures. Also, the material should be biocompatible, according to a USP Class VI approval or similar, thus having a ability to appropriately interact with the host biological organism into which it has been inserted, not generating any reactions from the organism.

The total probe assembly, including the fiber pig-tail with its optical connector termination, may be sterilized through methods like RF plasma sterilizing at 46° C. or ethylene-oxide atmosphere at 70° C. The tube material is thus preferably made from low susceptibility material like, but not limited to, polyimide, polytetrafluorethylene (Teflon), polyetheretherketone (PEEK) or titanium.

The titanium metal tube shows recognizable but low signature in magnetic resonance (MR) imaging. The polymer tube may be equipped with one or more ring shaped metallic markers for the position observation during MR imaging.

Different insertion situations call for different structural properties of the probe tube.

Tissue insertion requires a tube that possesses adequate stiffness to tolerate the insertion force without deformation or breakage. Relevant materials are polyimide, polyetheretherketone (PEEK) and titanium. Fiber-reinforced composite materials are potentially good future candidates due to their generally excellent strength. For this insertion situation the tip 3 of the probe should be sharp.

Insertion into cavities and natural tubes of the body as well as insertion through endoscopic needles and devices, may require stiffness different from that described above. The flexibility of the probe has to be adequate with respect to the ability to be guided along a 3-D route defined by the topography of the organ, blood vessel, etc. Possible materials are polytetrafluorethylene (Teflon), polyamide (Nylon), silicone, etc. In this case the flat or rounded tip solution will be preferred.

The assembly shown in FIG. 1 comprises the probe, constituted by the sheath tube 2 and the tip 3 sealing the tube, providing a hollow tube containing the fiber sensor 1. The tube is also sealed at the coupling 4,5 using an adhesive 10 between the tube 2 and the splicing sheath 4 providing a coupling to the related measuring systems.

The length of the tube will depend upon the application, but will typically have a length of 5–100 cm, the tube having an inner diameter being 0.3–0.7 mm allowing the fiber to move freely within the tube.

The fiber sensor 1 is coupled to a fiber pigtail 7 connected to corresponding measuring instruments in a splice 6 positioned in a per se known manner inside a stress reliever 5.

The splicing sheath 4 also envelopes the end of the fiber pigtail, said pigtail in this case comprising the optical fiber 7 spliced to the fiber sensor 1, a secondary coating 8 protecting the optical fiber and a pigtail jacket 9 also comprising kevlar fibers 11 for the protection of the optical fiber 7. Other types of splicing means may of course also be used within the scope of this invention.

As the tubing of the probe is terminated at splice between the fiber sensor and the fiber pigtail, there is no opening along the probe through which the fluids in the measuring object may pass when used inside a body. Thus the probe is not subject to leaks damaging the sensor, or at least disturbing the measurements, as would be the case with the sensor described in the abovementioned article by Y. Rao et al.

In an alternative and simpler assembly (not shown in the drawings) the sheath tube with tip and sensor fiber of the sensor probe is terminated directly into a standard optical connector.

A preferred use of the probe according to this invention is, as indicated above, during thermal therapies and for monitoring of body temperatures bedside, during surgery or in intensive care.

A particularly preferred use of the probe is in monitoring the temperature of the prostate gland and surrounding tissue during cryoblation surgery thereof to treat prostate carcinoma. The cryoablation surgical method and system is identical to that taught in U.S. Pat. No. 5,647,868 (fully incorporated herein by reference) except that temperature probes as described above with reference to FIG. 1 are used to monitor the temperature of the prostate gland instead of the temperature probes 36 disclosed therein; and that the ultrasonic imaging system 14, 16, 22, 24 is replaced with a magnetic resonance imaging system, well known per se in the art.

The invention claimed is:

1. A body compatible insertion probe for sensing distributed temperature during cryosurgery, the probe comprising a tube containing at least one optical fiber being inscribed with at least two Bragg gratings, the tube being sealed along its length and at its distal end, wherein the probe is comprised primarily of materials having low magnetic susceptibility and wherein a portion of the optical fiber housed within the tube comprises at least two Bragg gratings.

2. A probe according to claim 1, wherein the outer surface consists of a bio-compatible material according to a USP Class VI approval or similar.

3. A probe according to claim 1, wherein its distal end comprises a cutting edge tip.

4. A probe according to claim 1, wherein its distal end comprises a rounded tip.

5. A probe according to claim 1, wherein the magnetic susceptibility is less than 200 ppm, and preferably below 10 ppm.

6. A probe according to claim 5, wherein the tube and tip on its distal end is made from titanium.

7. A probe according to claim 5, wherein the tube and tip on its distal end is made from a polymer material, e.g. polyimide.

8. A probe according to claim 7, wherein the polymer tube is equipped with one or more metallic markers for the position observation during MR imaging.

9. A probe according to claim 1, wherein the optical fiber is loosely positioned in a tube so as to be able to expand and contract freely with changing temperatures.

10. A probe according to claim 9, wherein the fiber end is wedge cut.

11. A probe according to claim 1, wherein the fiber comprises two or more Bragg gratings distributed along the fiber so as to provide temperature measurements in different positions along the fiber.

12. A probe according to claim 1, wherein the tube is made from a material providing sufficient strength and stiffness to support direct insertion into soft biological tissues.

13. A probe according to claim 1, wherein the probe is provided with coupling means for coupling the optical fiber to a wavelength spectrum analyser for analysing the spectrum of the wavelengths being reflected from the Bragg gratings.

14. A cryosurgical apparatus comprising at least one cryoapplicator for cooling an area of a living body and at least one insertion probe as claimed in claim 1.

15. A cryosurgical apparatus as claimed in claim 14, further comprising magnetic resonance imaging apparatus.

16. A method of measuring temperature inside a body being subject to strong electromagnetic fields, e.g. during magnetic resonance imaging, comprising using an optical temperature probe according to claim 1.

17. A method of measuring temperature in medical applications during thermal therapies comprising using an optical temperature probe according to claim 1.

18. A method of measuring temperature inside a body being subject to strong electromagnetic fields, e.g. during magnetic resonance imaging, comprising using an optical probe according to claim 5.

19. A method for performing cryosurgery on a living body comprising measuring a temperature of a part of said living body using one or more insertion probes as claimed in claim 1.

20. A method of monitoring body temperature at bedside, during surgery or intensive care comprising using an optical temperature probe according to claim 1.

21. A method of performing cryosurgery on a living body comprising the steps:
    inserting one or more temperature insertion probes into said living body, said insertion probe(s) comprising a tube containing at least one optical fiber being inscribed with at least two Bragg gratings, the tube being sealed at its distal end, and wherein said temperature insertion probe(s) consist(s) of materials having low magnetic susceptibility, and wherein a portion of the optical fiber housed within the tube comprises at least two Bragg gratings; and
    sensing a distributed temperature of a part of said living body using said insertion probe(s).

22. A method as claimed in claim 21 further comprising the step of imaging said living body using magnetic resonance imaging.

23. A cryosurgical system for treating a part of a living body, the system comprising:
    one or more cryo-applicators for cryosurgically cooling said part of said living body;
    one or more temperature probes for insertion into said living body, said probe comprising a tube containing at least one optical fiber being inscribed with at least two Bragg gratings, the tube being sealed at its distal end, wherein said temperature probe(s) comprise(s) substantially materials having low magnetic susceptibility, and wherein a portion of the optical fiber housed within the tube comprises at least two Bragg gratings;
    magnetic resonance imaging apparatus for imaging said part of said living body; and
    a temperature display connected to said temperature probe(s) for displaying the temperature of said part of said living body or a surrounding part.

* * * * *